(12) United States Patent
Cordi et al.

(10) Patent No.: US 8,569,285 B2
(45) Date of Patent: Oct. 29, 2013

(54) DIHYDROBENZOXATHIAZEPINE COMPOUNDS, A PROCESS FOR THEIR PREPARATION AND PHARMACEUTICAL COMPOSITIONS CONTAINING THEM

(75) Inventors: Alexis Cordi, Suresnes (FR); Patrice Desos, Bois-Colombes (FR); Pierre Lestage, Le Celle Saint Cloud (FR); Laurence Danober, Montesson (FR)

(73) Assignee: Les Laboratoires Servier, Suresnes Cedex (FR)

( * ) Notice: Subject to any disclaimer, the term of this patent is extended or adjusted under 35 U.S.C. 154(b) by 176 days.

(21) Appl. No.: 13/200,045

(22) Filed: Sep. 15, 2011

(65) Prior Publication Data

US 2012/0071462 A1    Mar. 22, 2012

(30) Foreign Application Priority Data

Sep. 16, 2010   (FR) ..................................... 10 03683

(51) Int. Cl.
| | | |
|---|---|---|
| *A61P 25/08* | (2006.01) |
| *A61P 25/14* | (2006.01) |
| *A61P 25/18* | (2006.01) |
| *A61P 25/28* | (2006.01) |
| *A61K 31/554* | (2006.01) |
| *C07D 271/06* | (2006.01) |
| *C07D 291/08* | (2006.01) |
| *C07D 419/12* | (2006.01) |

(52) U.S. Cl.
USPC ........................................ 514/211.1; 540/552

(58) Field of Classification Search
USPC ........................................ 514/211.1; 540/552
See application file for complete search history.

(56) References Cited

FOREIGN PATENT DOCUMENTS

| WO | WO 99/42456 | 8/1999 |
| WO | WO 02/100865 | 12/2002 |
| WO | WO 2006/125972 | 11/2006 |

*Primary Examiner* — Brenda Coleman
(74) *Attorney, Agent, or Firm* — Hueschen and Sage

(57) ABSTRACT

Compounds of formula (I):

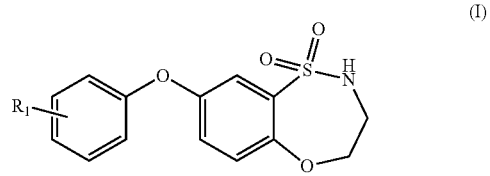

(I)

wherein $R_1$ represents a hydrogen atom or a heterocyclic, cyano, alkoxycarbonyl, alkylsulphonylaminoalkyl or N-hydroxycarboximidamide group.

Medicinal products containing the same which are useful as modulators of the AMPA receptor.

13 Claims, No Drawings

DIHYDROBENZOXATHIAZEPINE COMPOUNDS, A PROCESS FOR THEIR PREPARATION AND PHARMACEUTICAL COMPOSITIONS CONTAINING THEM

The present invention relates to new dihydrobenzoxathiazepine compounds, to a process for their preparation, to pharmaceutical compositions containing them and to the use thereof as positive allosteric modulators of AMPA receptors.

It has now been recognised that the excitatory amino acids, very especially glutamate, play a crucial role in the physiological processes of neuronal plasticity and in the mechanisms underlying learning and memory. Pathophysiological studies have clearly shown that a deficit in glutamatergic neurotransmission is closely linked to the development of Alzheimer's disease (Neuroscience and Biobehavioral Reviews, 1992, 16, 13-24; Progress in Neurobiology, 1992, 39, 517-545).

In addition, certain works have in recent years demonstrated the existence of sub-types of excitatory amino acid receptors and their functional interactions (Molecular Neuropharmacology, 1992, 2, 15-31).

Among those receptors, the AMPA (α-amino-3-hydroxy-5-methyl-4-isoxazole-propionic acid) receptor appears to be involved to the greatest extent in the phenomena of physiological neuronal excitability and, especially, in those phenomena involved in memorisation processes. For example, it has been shown that learning is associated with an increase in the binding of AMPA to its receptor in the hippocampus, one of the areas of the brain essential to processes of memory and cognition. Likewise, nootropic agents such as aniracetam have very recently been described as modulating the AMPA receptors of neuronal cells in a positive manner (J. Neurochemistry, 1992, 58, 1199-1204).

In the literature, compounds having a benzamide structure have been described as possessing this same mechanism of action and improving memory performance (Synapse, 1993, 15, 326-329). Compound BA 74, in particular, is the most active of those new pharmacological agents.

More recently, Patent Application WO 99/42456 describes benzothiadiazine and benzothiadiazepine compounds as modulators of AMPA receptors and Patent Application WO 02/100865 describes benzoxazepine compounds having facilitatory activity on AMPA flux.

The dihydrobenzoxathiazepine compounds to which the present invention relates are new and constitute powerful positive allosteric modulators of AMPA receptors.

More specifically, the present invention relates to compounds of formula (I):

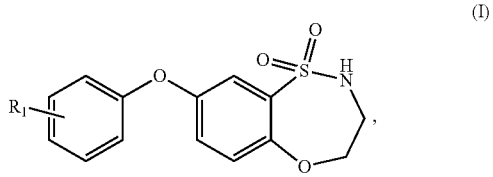

wherein $R_1$ represents a hydrogen atom, a cyano group, a linear or branched ($C_1$-$C_6$)alkoxycarbonyl group, a ($C_1$-$C_6$)alkylsulphonylamino-($C_1$-$C_6$)alkyl group in which the alkyl moieties are each linear or branched, an N-hydroxycarboximidamide group or a heterocyclic group, to their enantiomers and diastereoisomers, and also to addition salts thereof with a pharmaceutically acceptable acid or base, it being understood that the term "heterocyclic group" denotes a 5-membered monocyclic aromatic group containing one to four hetero atoms which are the same or different and which are selected from nitrogen, oxygen and sulphur, it optionally being possible for said heterocyclic group to be substituted by one or more substituents which are the same or different and which are selected from linear or branched ($C_1$-$C_6$)alkyl and linear or branched ($C_1$-$C_6$)polyhaloalkyl.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

Among the pharmaceutically acceptable bases there may be mentioned, without implying any limitation, sodium hydroxide, potassium hydroxide, triethylamine and tert-butylamine.

$R_1$ preferably represents a heterocyclic group.

$R_1$ more preferably represents a 5-membered monocyclic aromatic heterocyclic group containing at least one nitrogen atom, it optionally being possible for said group to be substituted by one or more substituents which are the same or different and which are selected from linear or branched ($C_1$-$C_6$)alkyl and linear or branched ($C_1$-$C_6$)polyhaloalkyl.

$R_1$ advantageously represents the groups pyrrolyl, pyrazolyl, imidazolyl, triazolyl, tetrazolyl, isoxazolyl, oxazolyl, isothiazolyl, thiazolyl, thiadiazolyl, dithiazolyl and oxadiazolyl, it optionally being possible for each of the groups to be substituted by one or more substituents which are the same or different and which are selected from linear or branched ($C_1$-$C_6$)alkyl and linear or branched ($C_1$-$C_6$)polyhaloalkyl.

More especially preferred are compounds wherein $R_1$ represents the groups oxadiazolyl and thiazolyl and, more especially the groups 1,2,4-oxadiazolyl and 1,3-thiazolyl, it optionally being possible for each of the preferred groups to be substituted by one or more substituents which are the same or different and which are selected from linear or branched ($C_1$-$C_6$)alkyl and linear or branched ($C_1$-$C_6$)polyhaloalkyl.

As substituents of the heterocyclic group, preference is given to a methyl group or a trifluoromethyl group.

The group $R_1$ is preferably in meta or para position of the phenoxy ring carrying it. Advantageously, the group $R_1$ is in meta position.

Preferred compounds according to the invention are:
8-[3-(5-methyl-1,2,4-oxadiazol-3-yl)phenoxy]-3,4-dihydro-2H-5,1,2-benzoxathiazepine 1,1-dioxide;
8-[3-(3-methyl-1,2,4-oxadiazol-5-yl)phenoxy]-3,4-dihydro-2H-5,1,2-benzoxathiazepine 1,1-dioxide.

Addition salts with a pharmaceutically acceptable acid or base of the preferred compounds of the invention form an integral part of the invention.

The invention relates also to a process for the preparation of compounds of formula (I) starting from the compound of formula (II):

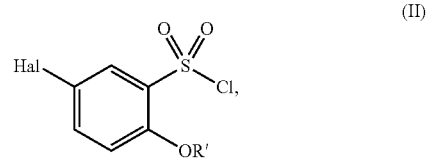

wherein Hal represents a halogen atom such as fluorine, chlorine or bromine and R' represents a linear or branched ($C_1$-$C_6$)alkyl group, which is reacted with 2-chloroethylamine in a basic medium to yield the compound of formula (III):

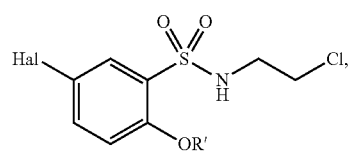
(III)

wherein Hal and R' are as defined hereinbefore, which is then subjected to the action of a boron-containing compound to yield the compound of formula (IV):

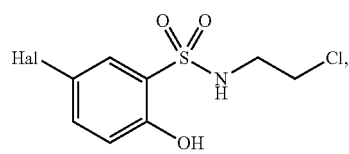
(IV)

wherein Hal is as defined hereinbefore, which is then cyclised to yield the compound of formula (V):

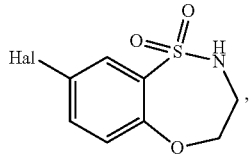
(V)

wherein Hal is as defined hereinbefore, which is subjected to a reaction protecting the nitrogen atom to yield the compound of formula (VI):

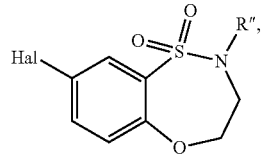
(VI)

wherein Hal is as defined hereinbefore and R" represents a protecting group for the amine function such as, for example, a tert-butyloxycarbonyl group, which is converted into a boronic acid to yield the compounds of formula (VII):

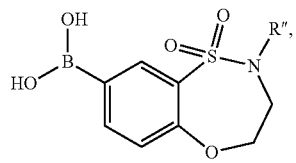
(VII)

wherein R" is as defined hereinbefore,
which is reacted with an alcohol of formula (VIII):

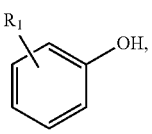
(VIII)

wherein $R_1$ is as defined for formula (I),
to yield the compound of formula (IX):

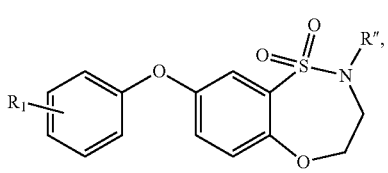
(IX)

wherein $R_1$ and R" are as defined hereinbefore;
which is then subjected to a reaction deprotecting the amine function to yield the compound of formula (I),
a variant in the preparation of the compounds of formula (I) consisting of hydrolysis of the compound of formula (VII) to yield the compound of formula (X):

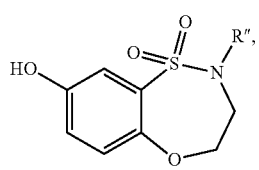
(X)

wherein R" is as defined hereinbefore,
which is reacted with a boronic acid compound of formula (XI):

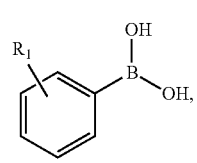
(XI)

wherein $R_1$ is as defined for formula (I),
to yield the compound of formula (IX),
which is then subjected to a reaction deprotecting the amine function to yield the compound of formula (I), another alternative in the preparation of the compounds of formula (I) consisting of using conventional chemical reactions, after preparation of the compounds of formula (IX), in order to subsequently change the substituent of the phenoxy ring,
which compound of formula (I) may then be purified according to a conventional separation technique, is converted, if desired, into its addition salts with a pharmaceutically acceptable acid or base and is separated, where appropriate, into its isomers, if they exist, according to a conventional separation technique.

The compounds of formulae (II), (VIII) and (XI) are commercially available or readily accessible to the person skilled in the art using conventional chemical reactions or chemical reactions described in the literature.

The compounds of formula (V) are new and also form part of the invention as synthesis intermediates for compounds of formula (I).

The compounds of formula (I) according to the invention have AMPA receptor-activating properties which make them of use in the treatment or prevention of disorders of memory and cognition that are associated with age, with syndromes of anxiety or depression, with progressive neurodegenerative diseases, with Alzheimer's disease, with Parkinson's disease, with Pick's disease, with Huntington's chorea, with Korsakoff's disease, with schizophrenia, with the sequelae of acute neurodegenerative diseases, with frontal lobe and subcortical dementias, with the sequelae of ischaemia and with the sequelae of epilepsy.

The invention relates also to pharmaceutical compositions comprising, as active ingredient, at least one compound of formula (I) with one or more appropriate, inert, non-toxic excipients. Among the pharmaceutical compositions according to the invention there may be mentioned more especially those that are suitable for oral, parenteral (intravenous or subcutaneous) or nasal administration, tablets or dragées, sublingual tablets, capsules, lozenges, suppositories, creams, ointments, dermal gels, injectable preparations and drinkable suspensions.

The useful dosage can be varied according to the nature and severity of the disorder, the administration route and also the age and weight of the patient and ranges from 0.01 to 1000 mg per day in one or more administrations.

The Examples that follow illustrate the invention but do not limit it in any way.

The starting materials used are products that are known or that are prepared according to known operating procedures.

The structures of the compounds described in the Examples were determined according to the usual spectrophotometric techniques (infrared, NMR, mass spectrometry).

The Preparations described hereinbelow yield starting compounds used in synthesis of compounds of the invention.

Preparation 1:
3-(5-methyl-1,2,4-oxadiazol-3-yl)phenol

Step A: N', 3-dihydroxybenzenecarboximidamide

To a suspension of 15.84 g (0.228 mol) of hydroxylamine hydrochloride in 75 ml of DMSO there are added 32 ml (0.228 mol) of triethylamine. The solution is stirred vigorously for 30 minutes and is then diluted with a small amount of THF. After stirring for 10 minutes, the triethylamine hydrochloride is filtered off and the residue is rinsed with THF. After the filtrate has been concentrated (evaporating off the THF), 10 g (83.9 mmol) of 3-hydroxybenzonitrile are added to the solution obtained. The solution is stirred at ambient temperature for 16 hours. After diluting with cold water, the mixture is extracted 3 times with ethyl acetate and the organic phase is washed with brine. The expected product is obtained after drying over $MgSO_4$ and evaporation.

Step B: 3-[N'-(acetyloxy)carbamimidoyl]phenyl acetate

To a suspension of 10.2 g (67 mmol) of the product obtained in Step A above in 150 ml of $CH_2Cl_2$ there are added 28 ml (0.201 mol) of triethylamine. 13.9 ml (0.147 mol) of acetic anhydride are added dropwise and the solution is stirred overnight at ambient temperature. After washing 3 times with water and then with brine, the organic phase is dried over $MgSO_4$ and evaporated. The solid obtained is taken up in isopropyl ether and then filtered and dried to yield the title compound.

Melting point: 128° C.
Elemental microanalysis:

|  | C | H | N |
|---|---|---|---|
| theoretical % | 55.93 | 5.12 | 11.86 |
| experimental % | 55.94 | 5.13 | 11.71 |

Step C: 3-(5-methyl-1,2,4-oxadiazol-3-yl)phenyl acetate

To a solution of 9.40 g (39.8 mmol) of the product obtained in Step B above in 300 ml of toluene there are added 150 mg of para-toluenesulphonic acid and the reaction mixture is heated at reflux, using a Dean-Stark system, for 12 hours. The title product is obtained after evaporating off the toluene using a rotary evaporator.

Melting point: 94° C.

Step D: 3-(5-methyl-1,2,4-oxadiazol-3-yl)phenol

A solution of 8.55 g (39.18 mmol) of the product obtained in Step C above in 120 ml of 1N HCl solution is heated at reflux for 90 minutes and is then left at ambient temperature overnight, with stirring. The precipitate is filtered off to yield the title product.

Melting point: 118° C.
Elemental microanalysis:

|  | C | H | N |
|---|---|---|---|
| theoretical % | 61.36 | 4.58 | 15.90 |
| experimental % | 61.44 | 4.55 | 15.82 |

Preparation 2: 3-(1,3-oxazol-2-yl)phenol

Step A: 2-(3-methoxyphenyl)-1,3-oxazole

A suspension containing 1.16 ml of 1-bromo-3-methoxybenzene (9.2 mmol), 2.12 ml of 2-(tributylstannanyl)-1,3-oxazole (5.9 mmol) and 276 mg (0.2 mmol) of tetrakis[triphenylphosphine]palladium in 50 ml of toluene is stirred overnight at reflux under argon. The toluene is evaporated off using a rotary evaporator, and the residue is then suspended in ethyl acetate. After filtering the suspension, the filtrate is evaporated to dryness and the crude product is purified by chromatography over silica gel, eluting with $CH_2Cl_2$ and then with $CH_2Cl_2$/acetone 98/2 to yield the title product in the form of an oil.

Step B: 3-(1,3-oxazol-2-yl)phenol

The product obtained in Step A above (250 mg, 1.13 mmol) is suspended in 10 ml of aqueous 48% HBr solution, and the reaction mixture is stirred overnight at 115° C. After cooling to ambient temperature, the mixture is poured into 10 ml of 10% $NaHCO_3$ solution. The pH is adjusted to 7 and the aqueous phase is extracted with ethyl acetate. The organic phase is washed (saturated NaCl) and dried ($MgSO_4$) to yield, after filtration and evaporation, the title product in the form of a white solid.

Preparation 3: [4-(5-methyl-1,2,4-oxadiazol-3-yl)phenyl]boronic acid

Step A: N'-hydroxy-4-iodobenzenecarboximidamide 17.3 g (249 mmol) of hydroxylamine hydrochloride and then 35 ml (251 mmol) of triethylamine are added to 80 ml of DMSO. A voluminous white precipitate forms, and the reaction mixture is diluted with a small amount of THF. After stirring for 1 hour, the precipitate is filtered off. The filtrate is collected and then transferred to a flask to which there are added 9.55 g (41.7 mmol) of 4-iodobenzonitrile. The reaction mixture is stirred overnight at ambient temperature and is then cooled in an ice bath and 200 mL of water are added. The precipitate is filtered off to yield the expected product.

Elemental microanalysis:

|  | C | H | N | I |
|---|---|---|---|---|
| theoretical % | 32.08 | 2.69 | 10.69 | 48.43 |
| experimental % | 32.05 | 2.77 | 10.55 | 47.46 |

Step B: N'-(acetyloxy)-4-iodobenzenecarboximidamide

To a suspension of the product obtained in Step A above (8.43 g, 32.17 mmol) in 200 ml of $CH_2Cl_2$ there are added 6.72 ml (48.2 mmol) of triethylamine. 3.34 ml (35.4 mmol) of acetic anhydride are added dropwise and the solution is stirred overnight at ambient temperature. After washing 3 times with water and then with brine, the organic phase is dried over $MgSO_4$ and evaporated. The solid obtained is taken up in isopropyl ether and then filtered to yield the title product.

Melting point: 139° C.

Step C: 3-(4-iodophenyl)-5-methyl-1,2,4-oxadiazole

To a solution of the product obtained in Step B above (9.7 g, 31.9 mmol) in 300 ml of toluene there are added 150 mg of para-toluenesulphonic acid and the reaction mixture is heated at reflux, using a Dean-Stark installation, for 24 hours. The mixture is evaporated to dryness and dried using a vacuum pump.

Melting Point: 91° C.

Step D: 5-methyl-3-[4-(4,4,5,5-tetramethyl-1,3,2-dioxaborolan-2-yl)phenyl]-1,2,4-oxadiazole To a solution of the product obtained in Step C above (500 mg, 1.74 mmol) in 5 ml of DMF there are added 510 mg (5.2 mmol) of potassium acetate and 577 mg (2.28 mmol) of bis(pinacolato)borane. The reaction mixture is degassed for 30 minutes using nitrogen and then 20 mg (0.09 mmol) of $Pd(OAc)_2$ are added. The reaction mixture is heated at 85° C. for 3 hours. After cooling to ambient temperature and then adding water, the reaction mixture is extracted with ethyl acetate. The organic phases are combined, washed (saturated NaCl) and dried ($MgSO_4$). The crude product is purified by chromatography over silica gel eluting with a mixture of heptane/ethyl acetate 7/3 to yield the expected product.

Melting point: 128° C.

Step E: [4-(5-methyl-1,2,4-oxadiazol-3-yl)phenyl]boronic acid

A suspension of the product obtained in Step D above (6.5 g, 22.7 mmol) in 230 ml of acetone is stirred for 24 hours in the presence of 18.4 g (86.0 mmol) of sodium meta-periodate and 70 ml of aqueous 1M ammonium acetate solution. The acetone is evaporated off using a rotary evaporator and, after adding water, the reaction mixture is extracted with ethyl acetate. The organic phases are combined, washed (NaCl) and dried ($MgSO_4$) to yield, after evaporation, the expected product.

Preparation 4: [3-(5-methyl-1,3,4-oxadiazol-2-yl)phenyl]boronic acid

Step A: N'-acetyl-3-iodobenzohydrazide

To a suspension of 3-iodobenzoic acid (2.0 g, 8.06 mmol) in 60 ml of THF there are added, in succession, DIPEA (1.83 ml, 10.48 mmol) and TBTU (2.59 g, 8.06 mmol). The reaction mixture is stirred overnight at ambient temperature. 1.19 g (16.12 mmol) of acetyl hydrazide are added and the reaction mixture is heated at reflux for 30 hours. After evaporation to dryness, the residue is taken up in water with a small amount of $CH_2Cl_2$; a thick precipitate forms, which is filtered off to yield the expected product.

Melting point: 178° C.

Step B: 2-(3-iodophenyl)-5-methyl-1,3,4-oxadiazole

The product obtained in Step A above (2.9 g, 9.54 mmol) is heated at 120° C. for 3 hours in 35 ml of $POCl_3$. After evaporation of $POCl_3$, the residue is taken up in toluene and the mixture is evaporated to dryness again. The residue from evaporation is dissolved in ethyl acetate and the organic phase is washed with, in succession, 10% $NaHCO_3$ solution, water and then brine. The organic phase is dried over $MgSO_4$ to yield, after evaporation, the expected product in the form of a creamy white solid.

Melting point: 115° C.

Step C: 2-methyl-5-[3-(4,4,5,5-tetramethyl-1,3,2-dioxaborolan-2-yl)phenyl]-1,3,4-oxadiazole The title product is obtained in accordance with the procedure described in Step D of Preparation 3 taking as starting material the compound described in Step B above instead of 3-(4-iodophenyl)-5-methyl-1,2,4-oxadiazole.
Melting point: 153° C.

Step D:
[3-(5-methyl-1,3,4-oxadiazol-2-yl)phenyl]boronic acid

The title product is obtained in accordance with the procedure described in Step E of Preparation 3, taking as starting material the compound described in Step C above instead of 5-methyl-3-[4-(4,4,5,5-tetramethyl-1,3,2-dioxaborolan-2-yl)phenyl]-1,2,4-oxadiazole.
Melting point: 254° C.

EXAMPLE 1

8-[3-(5-methyl-1,2,4-oxadiazol-3-yl)phenoxy]-3,4-dihydro-2H-5,1,2-benzoxathiazepine 1,1-dioxide Step A: 5-bromo-2-methoxybenzenesulphonyl chloride To chlorosulphonic acid (140 mL, 2 mol), cooled to 0-5° C., there added dropwise 35 ml (0.279 mol) of 4-bromoanisole. The solution is stirred for 30 minutes at 0° C. and then for about 16 hours at ambient temperature; it is poured slowly onto ice and is then stirred for a few more minutes. The white precipitate formed is filtered off and then washed with copious amounts of water.
Melting point: 107° C.

Step B: 5-bromo-N-(2-chloroethyl)-2-methoxybenzenesulphonamide

To a suspension of 13.4 g (0.115 mol) of 2-chloroethylamine hydrochloride in 150 ml of $CH_2Cl_2$ there are added 34 ml (0.241 mol) of triethylamine and then, dropwise, 30 g (0.105 mol) of the product obtained in Step A above dissolved in 200 ml of $CH_2Cl_2$. The solution is stirred for 2 hours at ambient temperature and is then washed with 1N HCl solution, water and brine. The organic phase is dried over $MgSO_4$ and evaporated. The solid is re-suspended in ethyl ether and filtered off to yield the title product.
Melting point: 150° C.

Step C: 5-bromo-N-(2-chloroethyl)-2-hydroxybenzenesulphonamide

To a suspension of 29.9 g (91 mmol) of the product obtained in Step B above in 450 ml of $CH_2Cl_2$ there are added dropwise, at ambient temperature, 200 mL (200 mmol) of 1M $BBr_3$ solution in $CH_2Cl_2$. After stirring for 30 minutes, the solution is poured onto an ice/water mixture, whilst continuing to stir. After separation and extracting once with $CH_2Cl_2$, the organic phase is washed with brine, dried over $MgSO_4$ and evaporated. The oily residue is triturated in heptane until crystallisation takes place. The title product is collected by filtration.
Melting point: 109° C.

Step D: tert-butyl[(5-bromo-2-hydroxyphenyl)sulphonyl](2-chloroethyl)-carbamate

To a solution containing 25.55 g (81.2 mmol) of the product obtained in Step C above, 17.72 g (81.2 mmol) of di-tert-butyl dicarbonate and 496 mg (4.06 mmol) of dimethylaminopyridine in 500 mL of $CH_2Cl_2$ there are added dropwise 11.32 g (81.2 mmol) of triethylamine dissolved in 200 ml of $CH_2Cl_2$. The mixture is stirred overnight at ambient temperature. The organic phase is washed (saturated NaCl), dried ($MgSO_4$) and evaporated using a rotary evaporator to yield the title product.

Step E:
8-bromo-3,4-dihydro-2H-5,1,2-benzoxathiazepine 1,1-dioxide 37 g (81 mmol) of the product obtained in Step D above are heated at reflux in the presence of 2.69 g (16 mmol) of KI and 33.6 g (240 mmol) of $K_2CO_3$ in 1.2 L of ethanol for about 18 hours. After cooling, the salts are filtered off and rinsed with acetone. After evaporation, the filtrate is taken up in water. The mixture is acidified with 1N HCl solution and then extracted 3 times with $CH_2Cl_2$. The organic phase is washed twice with brine, dried over $MgSO_4$ and evaporated. The residue obtained (~22 g) is then triturated in heptane, and then the mixture is allowed to separate in order to remove the heptane supernatant. The residue is again triturated in a heptane/isopropyl ether mixture to obtain a solid. After filtration, the product is rapidly dried and then ground in a mortar. The solid obtained is dissolved in heptane, stirred for about 1 hour and filtered to yield the expected product.
Melting point: 129° C.

Step F: tert-butyl 8-bromo-3,4-dihydro-2H-5,1,2-benzoxathiazepine-2-carboxylate 1,1-dioxide To a solution of 19.65 g (70.6 mmol) of the product obtained in Step E above and 259 mg (2 mmol) of DMAP in 200 ml of $CH_2Cl_2$ there are added dropwise 23.1 g (106 mmol) of di-tert-butyl dicarbonate dissolved in 125 ml of $CH_2Cl_2$. The reaction mixture is stirred at ambient temperature and then, after 3 hours, 100 mg of DMAP are added. The solution is stirred for 45 minutes. After washing twice with water and with brine, the organic phase is dried over $MgSO_4$ and evaporated. The residue from evaporation is triturated in heptane. The solid obtained is dissolved in heptane and stirred for 48 hours, resulting in a precipitate which is filtered to yield the title product.
Melting point: 119° C.

Step G: [2-(tert-butoxycarbonyl)-1,1-dioxido-3,4-dihydro-2H-5,1,2-benzoxathiazepin-8-yl]boronic acid To a solution of the product obtained in Step F above (21.6 g, 57.3 mmol) and 40 ml of triisopropyl borate in 210 ml of THF, cooled to −65° C. and under $N_2$, there are added dropwise 90 ml (143 mmol) of 1.6M nBuLi solution. The reaction mixture is stirred for 1 hour at −65° C. and allowed to return to ambient temperature. After stirring for 1 hour, the solution is cooled in an ice bath and hydrolysed by adding 320 ml of 0.5M HCl solution. After extracting 3 times with $CH_2Cl_2$, the organic phase is washed with brine, dried over $MgSO_4$ and evaporated. The residue is taken up in heptane and, after evaporation, is triturated in heptane and filtered to yield the title product.
Melting point: 197° C.

Step H: tert-butyl 8-[3-(5-methyl-1,2,4-oxadiazol-3-yl)phenoxy]-3,4-dihydro-2H-5,1,2-benzoxathiazepine-2-carboxylate 1,1-dioxide A suspension containing 2.5 g (7.28 mmol) of the product obtained in Step G above, 1.17 g (6.62 mmol) of the compound of Preparation 1, 1.61 ml (19.9 mmol) of pyridine, 1.8 g (9.9 mmol) of copper acetate and 8 g of 4 Å sieve in 125 ml of $CH_2Cl_2$ is stirred at ambient temperature in air for 20 hours. The sieve is filtered off and the filtrate is rinsed with 125 ml of a mixture of $CH_2Cl_2$/MeOH. Then 6 g of $SiO_2$ are added to the filtrate before evaporation to dryness. The crude product is purified by chromatography over silica gel eluting with a mixture of $CH_2Cl_2$/acetone 97/3 to yield the expected product in the form of a meringue.

Step I: 8-[3-(5-methyl-1,2,4-oxadiazol-3-yl)phenoxy]-3,4-dihydro-2H-5,1,2-benzoxathiazepine 1,1-dioxide A solution of 1.92 g (4.05 mmol) of the product obtained in Step H above is heated at 80° C. for 2 hours in 15 ml of 4N HCl solution in dioxane. The mixture is evaporated to dryness and dried in vacuo. The crude product is purified by chromatography over silica gel eluting with a mixture of $CH_2Cl_2$/AcOEt. The solid is taken up in isopropyl ether and filtered to yield the title product.

Melting point: 177° C.

EXAMPLE 2

8-[3-(1,3-thiazol-2-yl)phenoxy]-3,4-dihydro-2H-5,1,2-benzoxathiazepine 1,1-dioxide

Step A: tert-butyl 8-[3-(1,3-thiazol-2-yl)phenoxy]-3,4-dihydro-2H-5,1,2-benzoxathiazepine-2-carboxylate 1,1-dioxide The title product is obtained according to the protocol described in Step H of Example 1 using (3-thiazol-2-yl)phenol (the preparation of which is described in *Bioorg. Med. Chem.* 2003, 11(7), 1235-48) instead of the compound of Preparation 1.

Step B: 8-[3-(1,3-thiazol-2-yl)phenoxy]-3,4-dihydro-2H-5,1,2-benzoxathiazepine 1,1-dioxide The title product is obtained according to the protocol described in Step I of Example 1 using the compound obtained in Step A above instead of tert-butyl 8-[3-(5-methyl-1,2,4-oxadiazol-3-yl)phenoxy]-3,4-dihydro-2H-5,1,2-benzoxathiazepine-2-carboxylate 1,1-dioxide.

Melting point: 148° C.

Elemental Microanalysis:

|  | C | H | N | S |
|---|---|---|---|---|
| theoretical % | 54.53 | 3.77 | 7.48 | 17.13 |
| experimental % | 54.68 | 3.85 | 7.34 | 17.18 |

EXAMPLE 3

8-[3-(1,3-thiazol-5-yl)phenoxy]-3,4-dihydro-2H-5,1,2-benzoxathiazepine 1,1-dioxide

Step A: tert-butyl 8-[3-(1,3-thiazol-5-yl)phenoxy]-3,4-dihydro-2H-5,1,2-benzoxathiazepine-2-carboxylate 1,1-dioxide The title product is obtained according to the protocol described in Step H of Example 1 using (3-thiazol-5-yl)phenol (the preparation of which is described in *Bioorg. Med. Chem.* 2003, 11(7), 1235-48) instead of the compound of Preparation 1.

Step B: 8-[3-(1,3-thiazol-5-yl)phenoxy]-3,4-dihydro-2H-5,1,2-benzoxathiazepine 1,1-dioxide The title product is obtained according to the protocol described in Step I of Example 1 using the compound obtained in Step A above instead of tert-butyl 8-[3-(5-methyl-1,2,4-oxadiazol-3-yl)phenoxy]-3,4-dihydro-2H-5,1,2-benzoxathiazepine-2-carboxylate 1,1-dioxide.

Melting point: 60° C. (meringue)

Elemental Microanalysis:

|  | C | H | N | S |
|---|---|---|---|---|
| theoretical % | 54.53 | 3.77 | 7.48 | 17.13 |
| experimental % | 54.69 | 3.76 | 7.06 | 17.10 |

EXAMPLE 4

8-[3-(1,3-oxazol-2-yl)phenoxy]-3,4-dihydro-2H-5,1,2-benzoxathiazepine 1,1-dioxide

Step A: tert-butyl 8-[3-(1,3-oxazol-2-yl)phenoxy]-3,4-dihydro-2H-5,1,2-benzoxathiazepine-2-carboxylate 1,1-dioxide The title product is obtained according to the protocol described in Step H of Example 1 using the compound of Preparation 2 instead of the compound of Preparation 1.

Step B: 8-[3-(1,3-oxazol-2-yl)phenoxy]-3,4-dihydro-2H-5,1,2-benzoxathiazepine 1,1-dioxide The title product is obtained according to the protocol described in Step I of Example 1 using the compound obtained in Step A above instead of tert-butyl 8-[3-(5-methyl-1,2,4-oxadiazol-3-yl)phenoxy]-3,4-dihydro-2H-5,1,2-benzoxathiazepine-2-carboxylate 1,1-dioxide.

Melting point: 180° C.

Elemental Microanalysis:

|  | C | H | N | S |
|---|---|---|---|---|
| theoretical % | 56.98 | 3.94 | 7.82 | 8.95 |
| experimental % | 56.60 | 3.92 | 7.65 | 8.61 |

EXAMPLE 5

8-[4-(5-methyl-1,2,4-oxadiazol-3-yl)phenoxy]-3,4-dihydro-2H-5,1,2-benzoxathiazepine 1,1-dioxide

Step A: tert-butyl 8-hydroxy-3,4-dihydro-2H-5,1,2-benzoxathiazepine-2-carboxylate 1,1-dioxide A suspension of 4.7 g (13.69 mmol) of the product of Step G of Example 1 in a mixture of 90 ml of THF and 90 ml of water is stirred at ambient temperature in the presence of 5.27 g (34 mmol) of sodium perborate tetrahydrate overnight. The reaction mixture is diluted by adding saturated aqueous NH₄Cl solution and is then extracted with CH₂Cl₂. The organic phases are combined, washed (saturated NaCl), dried (MgSO₄) and evaporated using a rotary evaporator. The residue from evaporation is taken up and triturated in heptane in the presence of a few drops of isopropyl ether; a precipitate is formed which is filtered off to yield the expected product.

Melting point: 143° C.

Step B: tert-butyl 8-[4-(5-methyl-1,2,4-oxadiazol-3-yl)phenoxy]-3,4-dihydro-2H-5,1,2-benzoxathiazepine-2-carboxylate 1,1-dioxide The title product is obtained according to the protocol described in Step H of Example 1 using the compound of Preparation 3 instead of the compound of Preparation 1.

Step C: 8-[4-(5-methyl-1,2,4-oxadiazol-3-yl)phenoxy]-3,4-dihydro-2H-5,1,2-benzoxathiazepine 1,1-dioxide The title product is obtained according to the protocol described in Step I of Example 1 using the compound obtained in Step B above instead of tert-butyl 8-[3-(5-methyl-1,2,4-oxadiazol-3-yl)phenoxy]-3,4-dihydro-2H-5,1,2-benzoxathiazepine-2-carboxylate 1,1-dioxide.

Melting point: 171° C.

Elemental Microanalysis:

|  | C | H | N | S |
|---|---|---|---|---|
| theoretical % | 54.69 | 4.05 | 11.25 | 8.59 |
| experimental % | 54.81 | 4.07 | 10.96 | 8.54 |

EXAMPLE 6

8-[3-(5-methyl-1,3,4-oxadiazol-2-yl)phenoxy]-3,4-dihydro-2H-5,1,2-benzoxathiazepine 1,1-dioxide Step A: tert-butyl 8-[3-(5-methyl-1,3,4-oxadiazol-2-yl)phenoxy]-3,4-dihydro-2H-5,1,2-benzoxathiazepine-2-carboxylate 1,1-dioxide The title product is obtained according to the protocol described in Step H of Example 1 by reacting the product obtained in Step A of Example 5 with the compound of Preparation 4 instead of the compound of Preparation 1.

Step B: 8-[3-(5-methyl-1,3,4-oxadiazol-2-yl)phenoxy]-3,4-dihydro-2H-5,1,2-benzoxathiazepine 1,1-dioxide The title product is obtained according to the protocol described in Step I of Example 1 using the compound obtained in Step A above instead of tert-butyl 8-[3-(5-methyl-1,2,4-oxadiazol-3-yl)phenoxy]-3,4-dihydro-2H-5,1,2-benzoxathiazepine-2-carboxylate 1,1-dioxide.

Melting point: 192° C.

EXAMPLE 7

Ethyl 3-[(1,1-dioxido-3,4-dihydro-2H-5,1,2-benzoxathiazepin-8-yl)oxy]benzoate

Step A: tert-butyl 8-[3-(ethoxycarbonyl)phenoxy]-3,4-dihydro-2H-5,1,2-benzoxathiazepine-2-carboxylate 1,1-dioxide The title product is obtained according to the protocol described in Step H of Example 1 reacting the product obtained in Step A of Example 5 with [3-(ethoxycarbonyl)phenyl]-boronic acid.

Step B: Ethyl 3-[(1,1-dioxido-3,4-dihydro-2H-5,1,2-benzoxathiazepin-8-yl)oxy]-benzoate The title product is obtained according to the protocol described in Step I of Example 1 using the compound obtained in Step A above instead of tert-butyl 8-[3-(5-methyl-1,2,4-oxadiazol-3-yl)phenoxy]-3,4-dihydro-2H-5,1,2-benzoxathiazepine-2-carboxylate 1,1-dioxide.

Melting point: 120° C.

Elemental Microanalysis:

|  | C | H | N | S |
|---|---|---|---|---|
| theoretical % | 56.19 | 4.72 | 3.85 | 8.82 |
| experimental % | 55.71 | 4.70 | 4.07 | 9.02 |

EXAMPLE 8

3-[(1,1-dioxido-3,4-dihydro-2H-5,1,2-benzoxathiazepin-8-yl)oxy]benzonitrile

Step A: tert-butyl 8-(3-cyanophenoxy)-3,4-dihydro-2H-5,1,2-benzoxathiazepine-2-carboxylate 1,1-dioxide The title product is obtained according to the protocol described in Step H of Example 1 reacting the product obtained in Step A of Example 5 with (3-cyanophenyl)boronic acid.

Step B: 3-[(1,1-dioxido-3,4-dihydro-2H-5,1,2-benzoxathiazepin-8-yl)oxy]-benzonitrile The title product is obtained according to the protocol described in Step I of Example 1 using the compound obtained in Step A above instead of tert-butyl 8-[3-(5-methyl-1,2,4-oxadiazol-3-yl)phenoxy]-3,4-dihydro-2H-5,1,2-benzoxathiazepine-2-carboxylate.

Melting point: 131° C.

Elemental Microanalysis:

|  | C | H | N | S |
|---|---|---|---|---|
| theoretical % | 56.95 | 3.82 | 8.86 | 10.14 |
| experimental % | 56.66 | 3.88 | 8.64 | 9.98 |

EXAMPLE 9

N-{3-[(1,1-dioxido-3,4-dihydro-2H-5,1,2-benzoxathiazepin-8-yl)oxy]-benzyl}methanesulphonamide

Step A: tert-butyl 8-(3-{[(methylsulphonyl)amino]methyl}phenoxy)-3,4-dihydro-2H-5,1,2-benzoxathiazepine-2-carboxylate 1,1-dioxide The title product is obtained according to the protocol described in Step H of Example 1 reacting the product obtained in Step A of Example 5 with (3-{[(methylsulphonyl)-amino]methyl}phenyl)boronic acid.

Step B: N-{3-[(1,1-dioxido-3,4-dihydro-2H-5,1,2-benzoxathiazepin-8-yl)oxy]-benzyl}methanesulphonamide The title product is obtained according to the protocol described in Step I of Example 1 using the compound obtained in Step A above instead of tert-butyl 8-[3-(5-methyl-1,2,4-oxadiazol-3-yl)phenoxy]-3,4-dihydro-2H-5,1,2-benzoxathiazepine-2-carboxylate 1,1-dioxide.
Melting point: 57-60° C.

EXAMPLE 10

8-phenoxy-3,4-dihydro-2H-5,1,2-benzoxathiazepine 1,1-dioxide

Step A: tert-butyl 8-phenoxy-3,4-dihydro-2H-5,1,2-benzoxathiazepine-2-carboxylate 1,1-dioxide The title product is obtained according to the protocol described in Step H of Example 1 reacting the product obtained in Step A of Example 5 with phenylboronic acid.

Step B: 8-phenoxy-3,4-dihydro-2H-5,1,2-benzoxathiazepine 1,1-dioxide

The title product is obtained according to the protocol described in Step I of Example 1 using the compound obtained in Step A above instead of tert-butyl 8-[3-(5-methyl-1,2,4-oxadiazol-3-yl)phenoxy]-3,4-dihydro-2H-5,1,2-benzoxathiazepine-2-carboxylate 1,1-dioxide.
Melting point: 110° C.

EXAMPLE 11

3-[(1,1-dioxido-3,4-dihydro-2H-5,1,2-benzoxathiazepin-8-yl)oxy]-N'-hydroxybenzenecarboximidamide The title product is obtained according to the protocol described in Step A of Preparation 1 using the compound of Example 8 instead of 3-hydroxybenzonitrile.
Melting point: 163-166° C.
Elemental Microanalysis:

|  | C | H | N | S |
|---|---|---|---|---|
| theoretical % | 51.57 | 4.33 | 12.03 | 9.18 |
| experimental % | 51.27 | 4.42 | 11.62 | 9.31 |

EXAMPLE 12

8-{3-[5-(trifluoromethyl)-1,2,4-oxadiazol-3-yl]phenoxy}-3,4-dihydro-2H-5,1,2-benzoxathiazepine 1,1-dioxide To a suspension of the compound of Example 11 (800 mg, 2.29 mmol) in 15 ml of $CH_2Cl_2$ there are added 958 μl (6.87 mmol) of triethylamine and then 701 μl (5.04 mmol) of trifluoroacetic anhydride dropwise. After stirring for 1 hour at ambient temperature, the reaction mixture is washed with water and then with saturated NaCl solution and is dried over $MgSO_4$. The crude product is purified by chromatography over silica gel eluting with $CH_2Cl_2$ to yield the expected product in the form of a meringue.
Elemental Microanalysis:

|  | C | H | N | S |
|---|---|---|---|---|
| theoretical % | 47.78 | 2.83 | 9.83 | 7.50 |
| experimental % | 47.66 | 3.18 | 9.59 | 7.69 |

EXAMPLE 13

8-[3-(3-methyl-1,2,4-oxadiazol-5-yl)phenoxy]-3,4-dihydro-2H-5,1,2-benzoxathiazepine 1,1-dioxide

Step A: 3-[(1,1-dioxido-3,4-dihydro-2H-5,1,2-benzoxathiazepin-8-yl)oxy]benzoic acid A suspension of 1.0 g (2.23 mmol) of the product obtained in Step A of Example 7 in 20 ml of 1N NaOH solution and 1 ml of THF is stirred for 3 hours at 100° C. After cooling to ambient temperature, the reaction mixture is acidified by slowly adding 1N HCl solution. The white precipitate is filtered off and dried to yield the expected product.

Step B: 3-[(1,1-dioxido-3,4-dihydro-2H-5,1,2-benzoxathiazepin-8-yl)oxy]-N-[(1Z)—N-hydroxyethanimidoyl]benzamide To a suspension of the product obtained in Step A above (540 mg, 1.61 mmol) in 10 ml of $CH_2Cl_2$ there are added, in succession, 516 mg (1.61 mmol) of TBTU and then 364 μl (2.09 mmol) of DIEA. After stirring for 20 minutes, 120 mg (1.61 mmol) of N-hydroxyacetamidine are added and the reaction mixture is stirred for 1.5 hours at ambient temperature. The reaction mixture is washed with water and then with saturated NaCl solution, dried ($MgSO_4$) and evaporated to dryness. The residue is taken up in $CH_2Cl_2$; a white precipitate forms which is filtered off to yield the expected product.

Step C: 8-[3-(3-methyl-1,2,4-oxadiazol-5-yl)phenoxy]-3,4-dihydro-2H-5,1,2-benzoxathiazepine 1,1-dioxide To a solution of 390 mg (0.99 mmol) of the product obtained in Step B above in 50 ml of toluene there are added 35 mg of para-toluenesulphonic acid and the reaction mixture is heated at reflux using a Dean-Stark system for 12 hours. After evaporation, the crude reaction product is purified over silica gel eluting with a mixture of $CH_2Cl_2$/AcOEt 9/1 to yield the expected product.
Melting point: 140° C.

Elemental Microanalysis:

|  | C | H | N | S |
|---|---|---|---|---|
| theoretical % | 54.69 | 4.05 | 11.25 | 8.59 |
| experimental % | 54.78 | 4.11 | 11.00 | 8.70 |

Pharmacological Study

EXAMPLE A

Study of the Effect of Compounds on Membrane Depolarisation Brought about by AMPA in Primary Cultures of Rat Neurons The test comprises the in vitro measurement, by means of fluorescence, of the membrane depolarisation brought about in cultured rat embryonic neurons by the joint action of AMPA and the compound under test, compared to the action of AMPA alone. The brain cells are placed in culture and kept in a cell culture incubator for 18 days. After incubation, the culture medium is withdrawn and replaced with fluorescent probe loading medium for measurement of the membrane potential (20 µl; membrane potential kit from Molecular Devices) and left at ambient temperature for 1 hour. The base fluorescence of the wells is read (FDSS apparatus from Hamamatsu) and the cells are then injected with AMPA (20 µl; concentration range: from 3 to 100 µM) and the action of the AMPA is measured kinetically. The test compound is then introduced into the wells (20 µl; in a concentration range crossed with that of AMPA) and the action of the compound is measured kinetically. At the end of each of the two periods of kinetic measurement, the result for each well is the average reading over the final 15 seconds of the period. The curves are plotted of the effect of AMPA at the various concentrations of compound. For each concentration of compound, the result is the area under the AMPA curve at that concentration, and the $EC_{2X}$ (the concentration of compound which doubles the membrane potential brought about by AMPA) is calculated.

The compounds of the invention greatly potentiate the excitatory effects of AMPA. By way of example, the compounds of Example 1 and Example 13 have an $EC_{2X}$ of 5 and 18 µM, respectively.

EXAMPLE B

Object Recognition in the CD1 Mouse

The object recognition test (Behav. Brain Res., 1988, 31, 47-59) is based on the spontaneous exploratory activity of the animal and has the characteristics of episodic memory in humans. This memory test is sensitive to ageing (Eur. J. Pharm. 1997, 325, 173-180) and to cholinergic dysfunctions (Pharm. Biochem. Behav., 1996, 53(2), 277-283) and is based on the differences in the exploration of 2 objects—one familiar, the other new. The test procedure, which has been adapted for the CD1 mouse, comprises 3 phases which take place in the same test enclosure. During the first phase, which lasts 30 minutes, the mice are habituated to the environment (habituation phase). During the second phase, which takes place the next day, two identical objects are placed in the enclosure and the mouse is free to explore them (familiarisation phase). Once the total duration of that exploration has reached 20 seconds, the mouse is taken out of the enclosure. In the course of the third phase (5 minutes, recall phase), 6 hours later, one of the same objects is re-presented (acquiring the status of a "familiar" object), as well as a further object ("new" object). The duration of exploration, expressed in seconds, is timed for each of the two objects. The control animals, which have previously been given the carrier by the oral route 60 minutes before the familiarisation phase, explore the "familiar" object and the "new" object for an equivalent period during the recall phase, which indicates that the object previously presented has been forgotten. Animals having received a compound that facilitates mnemocognition explore the new object preferentially, which indicates that the memory of the object previously presented has been retained.

The results obtained with the compounds of the present invention show that, at doses of 0.3, 1 and 3 mg/kg PO, there is significantly more exploration of the new object than of the familiar object, with doubling and even trebling of the exploration time for the "new" object compared to the "familiar" object, which indicates that the compounds of the invention greatly enhance memorisation.

EXAMPLE C

Pharmaceutical Composition

Formula for the preparation of 1000 tablets each containing 10 mg of 8-[3-(5-methyl-1,2,4-oxadiazol-3-yl)phenoxy]-3,4-dihydro-2H-5,1,2-benzoxathiazepine 1,1-dioxide

| (Example 1) | 10 g |
|---|---|
| Hydroxypropylcellulose | 2 g |
| Wheat starch | 10 g |
| Lactose | 100 g |
| Magnesium stearate | 3 g |
| Talc | 3 g |

The invention claimed is:

1. A compound selected from those of formula (I):

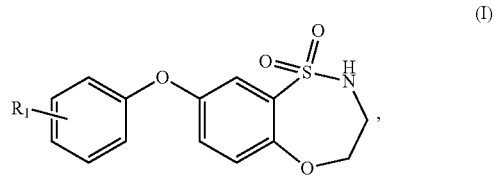

wherein $R_1$ represents a hydrogen atom, a cyano group, a linear or branched ($C_1$-$C_6$)alkoxycarbonyl group, a ($C_1$-$C_6$) alkylsulphonylamino-($C_1$-$C_6$)alkyl group in which the alkyl moieties may each be linear or branched, an N-hydroxycarboximidamide group or a heterocyclic group,
   its enantiomers and diastereoisomers, and addition salts thereof with a pharmaceutically acceptable acid or base,
   wherein the term "heterocyclic group" means a 5-membered monocyclic aromatic group having one to four hetero atoms which may be the same or different and which are selected from nitrogen, oxygen and sulphur, wherein the heterocyclic group may be optionally substituted by one or more substituents selected from linear or branched ($C_1$-$C_6$)alkyl and linear or branched ($C_1$-$C_6$) polyhaloalkyl.

2. The compound of claim 1, wherein $R_1$ represents a heterocyclic group.

3. The compound of claim 1, wherein $R_1$ represents a 5-membered monocyclic aromatic heterocyclic group having at least one nitrogen atom, which heterocyclic group may be optionally substituted by one or more substituents selected from linear or branched ($C_1$-$C_6$)alkyl and linear or branched ($C_1$-$C_6$)polyhaloalkyl.

4. The compound of claim 1, wherein $R_1$ represents a pyrrolyl, pyrazolyl, triazolyl, tetrazolyl, isoxazolyl, oxazolyl, isothiazolyl, thiazolyl, thiadiazolyl, dithiazolyl or oxadiazolyl group, which groups may be optionally substituted by, one or more substituents selected from linear or branched ($C_1$-$C_6$)alkyl and linear or branched ($C_1$-$C_6$)polyhaloalkyl.

5. The compound of claim 1, wherein $R_1$ represents a thiazolyl or oxadiazolyl group, which groups may be optionally substituted by one or more substituents selected from linear or branched ($C_1$-$C_6$)alkyl and linear or branched ($C_1$-$C_6$)polyhaloalkyl.

6. The compound of claim 1, wherein $R_1$ represents a 1,3-thiazolyl or 1,2,4-oxadiazolyl group, which groups may be optionally substituted by one or more substituents selected from linear or branched ($C_1$-$C_6$)alkyl and linear or branched ($C_1$-$C_6$)polyhaloalkyl.

7. The compound of claim 1, wherein $R_1$ represents a 1,3-thiazolyl or 1,2,4-oxadiazolyl group substituted by a methyl or trifluoromethyl group.

8. The compound of claim 1, wherein is in the meta position of the phenoxy ring carrying it.

9. The compound of claim 1, which is selected from:
   8-[3-(5-methyl-1,2,4-oxadiazol-3-yl)phenoxy]-3,4-dihydro-2H-5,1,2-benzoxathiazepine 1,1-dioxide;
   8-[3-(3-methyl-1,2,4-oxadiazol-5-yl)phenoxy]-3,4-dihydro-2H-5,1,2-benzoxathiazepine 1,1-dioxide;

its enantiomers and diastereoisomers, and addition salts thereof with a pharmaceutically acceptable acid or base.

10. A compound selected from those of formula (V):

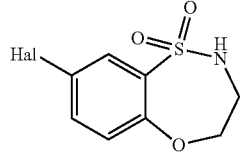

(V)

wherein Hal represents a halogen atom.

11. A pharmaceutical composition comprising as active ingredient a compound of claim 1 in combination with one or more inert, non-toxic, pharmaceutically acceptable carriers.

12. A method of treating a condition selected from disorders of memory and cognition that are associated with age, with syndromes of anxiety or depression, with progressive neurodegenerative diseases, with Alzheimer's disease, with Parkinson's disease, with Pick's disease, with Huntington's chorea, with Korsakoff's disease, with schizophrenia, with the sequelae of acute neurodegenerative diseases, with frontal lobe and subcortical dementias, with the sequelae of ischaemia and with the sequelae of epilepsy in a subject in need thereof, comprising administration of an effective amount of a compound of claim 1.

13. A compound according to claim 10 wherein Hal represents fluorine, chlorine or bromine.

* * * * *

UNITED STATES PATENT AND TRADEMARK OFFICE
CERTIFICATE OF CORRECTION

PATENT NO. : 8,569,285 B2  Page 1 of 1
APPLICATION NO. : 13/200045
DATED : October 29, 2013
INVENTOR(S) : Alexis Cordi et al.

It is certified that error appears in the above-identified patent and that said Letters Patent is hereby corrected as shown below:

In the Claims

Claim 8, Column 19, Line 26: "wherein is in the meta" should be
--wherein $R_1$ is in the meta--.

Signed and Sealed this
Fourteenth Day of January, 2014

Michelle K. Lee
*Deputy Director of the United States Patent and Trademark Office*